(12) United States Patent
Rosenzweig et al.

(10) Patent No.: US 11,464,495 B2
(45) Date of Patent: Oct. 11, 2022

(54) ADAPTIVE CLUTTER FILTERING IN ACOUSTIC RADIATION FORCE-BASED ULTRASOUND IMAGING

(71) Applicant: Siemens Medical Solutions USA, Inc., Malvern, PA (US)

(72) Inventors: Stephen J. Rosenzweig, Seattle, WA (US); Stirling Dodd, Monroe, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1248 days.

(21) Appl. No.: 15/919,903

(22) Filed: Mar. 13, 2018

(65) Prior Publication Data

US 2019/0282212 A1    Sep. 19, 2019

(51) Int. Cl.
*A61B 8/08* (2006.01)
*A61B 8/00* (2006.01)

(52) U.S. Cl.
CPC .......... *A61B 8/5276* (2013.01); *A61B 8/461* (2013.01); *A61B 8/485* (2013.01); *A61B 8/5207* (2013.01)

(58) Field of Classification Search
CPC ....... A61B 8/5276; A61B 8/461; A61B 8/485; A61B 8/5207
See application file for complete search history.

(56) References Cited

U.S. PATENT DOCUMENTS 8,465,433 B2  6/2013 Zwirn
9,883,852 B2  2/2018 Doherty et al.
2006/0241451 A1  10/2006 Nakaya et al.
2014/0276049 A1  9/2014 Doherty et al.
2015/0272547 A1 * 10/2015 Freiburger ............... A61B 8/54 600/438
2017/0042511 A1 * 2/2017 Labyed ................ A61B 8/5207
2017/0245832 A1  8/2017 Kawata et al.
2017/0296150 A1  10/2017 Rosenzweig et al.

FOREIGN PATENT DOCUMENTS

JP    2015522385       8/2015
JP    2018093899     * 12/2016
JP    2019535448      12/2019
WO   WO-2006123742 A1 * 11/2006 ............. A61B 8/463
WO    2017144716       8/2017

OTHER PUBLICATIONS

Doherty, Joshua R., et al. "Harmonic tracking of acoustic radiation force-induced displacements" IEEE transactions on ultrasonics, ferroelectrics, and frequency control 60.11 (2013): 2347-2358.
Song, Pengfei, et al. "Improved shear wave motion detection using pulse-inversion harmonic imaging with a phased array transducer." IEEE transactions on medical imaging 32.12 (2013): 2299-2310.
Song, Pengfei, et al. "Shear wave elastography on the GE LOGIQ E9 with Comb-push Ultrasound Shear Elastography (CUSE) and time aligned sequential tracking (TAST)." Ultrasonics Symposium (IUS), 2014 IEEE International. IEEE, 2014.

* cited by examiner

*Primary Examiner* — Rochelle D Turchen

(57) ABSTRACT

For clutter reduction in ultrasound elasticity imaging, the contribution of clutter to different frequency components (e.g., the transmit fundamental and the propagation generated second harmonic) is different. As a result, a difference in displacements determined at the different frequency bands is used to reduce clutter contribution to displacements used for elasticity imaging.

9 Claims, 7 Drawing Sheets

ADAPTIVE CLUTTER FILTERING IN ACOUSTIC RADIATION FORCE-BASED ULTRASOUND IMAGING

BACKGROUND

The present embodiments relate to elasticity imaging with ultrasound using acoustic radiation force (ARF). Ultrasound elasticity imaging includes different imaging techniques that characterize the elastic properties of tissue, such as acoustic radiation force impulse (ARFI) imaging or shear wave elasticity imaging (SWEI). These techniques characterize structure and/or pathology.

One significant noise source is ultrasonic noise from other structures (e.g., the body wall), commonly referred to as clutter. During beamforming, the data contains a combination of received echoes from both the tissue of interest and other structures. Using the data to track displacements for elasticity imaging, the estimated displacement is therefore a combination of displacements in the other structures and the tissue of interest. The displacements from other regions are considered noise.

One method of separating the valid displacement signal from the noise is to use harmonic tracking. Harmonic tracking is generally effective at acoustically separating signals from the other structure and the tissue of interest since the received echoes at the harmonic are preferentially generated in the region of the high pressure in the field, which typically corresponds to the tissue of interest. Other methods include synthesizing shear wave propagation from multiple tracking transmits, synthesizing with time aligned sequential tracking, or tracking concurrently using a broad acoustic transmit and parallel receive beamforming. In these methods, harmonic tracking improves the localization of the received echoes to the liver, but some of the received echoes still come from the body wall. For patients with relatively high body-mass index, a greater proportion of the received echoes are clutter even with harmonic tracking.

SUMMARY

By way of introduction, the preferred embodiments described below include methods, instructions, and systems for clutter reduction in ultrasound elasticity imaging. The contribution of clutter to different frequency components (e.g., the transmit fundamental and the propagation generated second harmonic) is different. As a result, a difference in displacements determined at the different frequency bands is used to reduce clutter contribution to displacements used for elasticity imaging.

In a first aspect, a method is provided for clutter reduction in elasticity imaging with an ultrasound scanner. Acoustic radiation force is transmitted from a transducer of the ultrasound scanner to tissue of a patient. The tissue responds to stress caused by the acoustic radiation force. The ultrasound scanner transmits a sequence of ultrasound pulses and receives echoes responsive to the ultrasound pulses of the sequence. Harmonic and fundamental components of the ultrasound echoes are isolated. First displacements of the harmonic components of the ultrasound echoes and second displacements of the fundamental components of the ultrasound echoes are determined. Combined displacements are formed from a subtraction of a difference from the first displacements. The difference is of the first displacements from the second displacements. An elasticity is estimated from the combined displacements, and an image of the elasticity is generated.

In a second aspect, a method is provided for clutter reduction in elasticity imaging with an ultrasound scanner. Displacements are independently determined from harmonic and other frequency components of received signals in tracking tissue movement in response to acoustic radiation force. The displacements from the harmonic and other frequency components are combined. The combination weights based on spatial region from which the received signals originated where the harmonic or other frequency components are stronger. Elasticity is estimated from the combined displacements, and an image of the elasticity is generated.

In a third aspect, a system is provided for clutter reduction in elasticity imaging. A transmit beamformer is configured to transmit an acoustic radiation force pulse and tracking pulses. The tracking pulses have inverted polarities. A receive beamformer is configured to receive signals interleaved with the tracking pulses. A filter is configured to output even harmonic information based on a sum of receive signals from the tracking pulses with the inverted polarities and to output fundamental information based on the receive signals. An image processor is configured to detect displacements of tissue responding to the acoustic radiation force from the even harmonic and fundamental information and to generate an elasticity from a compound of the displacements from the even harmonic and fundamental information. A display is configured to display the elasticity.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Acoustic radiation force (ARF)-based ultrasound imaging uses adaptive clutter filtering. Harmonic tracking of displacements helps to localize the displacements, but a portion of the signal still originates from the other structures in certain imaging scenarios (e.g., elasticity imaging of the liver where clutter from the body wall exists). When utilizing harmonic tracking, displacements are independently estimated with the fundamental component of the received echoes and the harmonic component of the received echoes. Displacement estimates from the fundamental and harmonic signals are combined in a way further reducing clutter noise compared to solely using harmonic tracking. The proportion of the signal from other structure and the tissue of interest are different in the fundamental signal compared to the harmonic signal. Both the fundamentally and harmonically tracked displacement data preferentially weight displacements from regions of the tissue of interest where the echoes from either the fundamental or harmonic signal are stronger. By combining displacement estimates from the fundamental and harmonic signals, the noise source may be reduced. Noise sources that corrupt displacement estimates are further reduced as compared to harmonic tracking, providing for more robust quantification of tissue stiffness.

Figure 1:
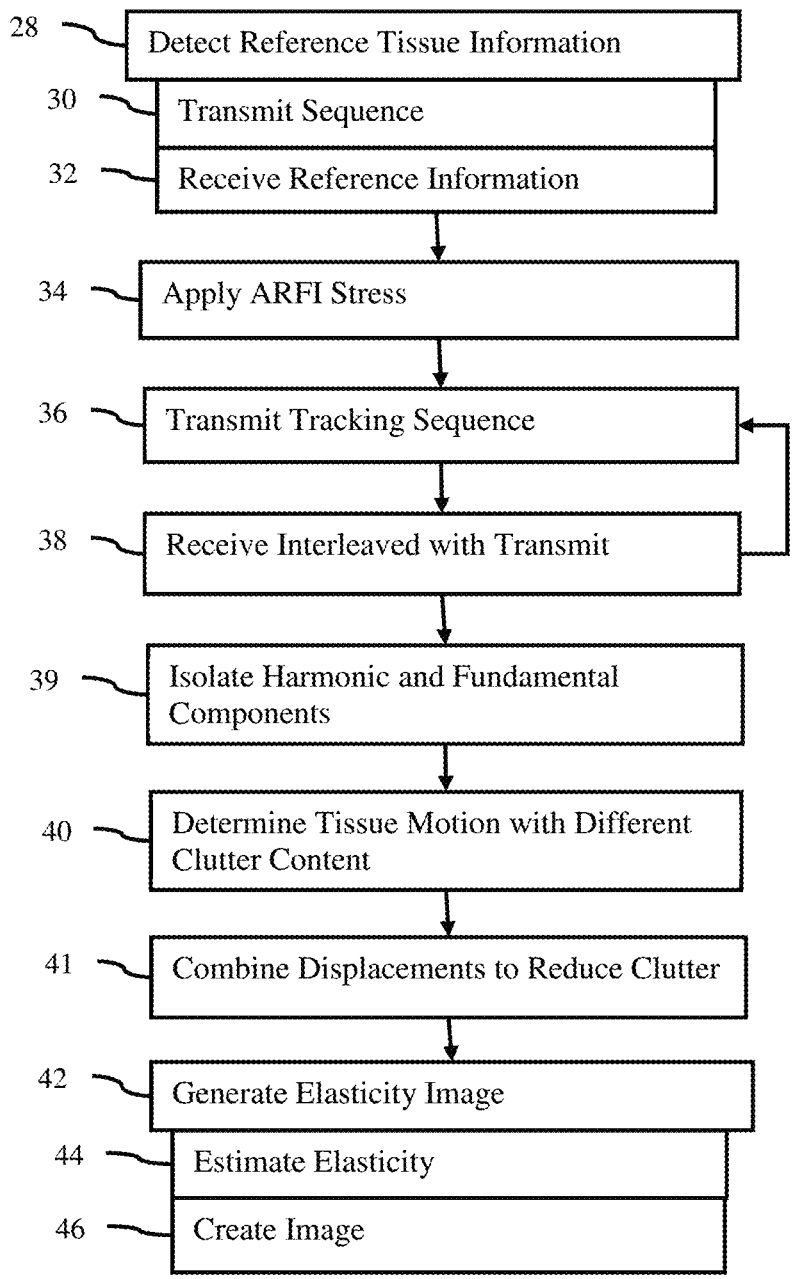
FIG. 1 is a flow chart diagram of one embodiment of a method for clutter reduction in elasticity imaging.

FIG. 1 shows one embodiment of a method for clutter reduction in elasticity imaging with an ultrasound scanner. Using any transmit and/or receive technique, receive signals at different frequency bands are created. Displacements are calculated for each frequency band. The displacements are combined in a way to reduce clutter. To further improve the localization of the estimated displacement to within the tissue of interest (e.g., liver), adaptive clutter filtering combines displacements estimated from both the different frequency bands while using harmonic tracking. An elasticity image is generated from the combined displacements, providing better images of the patient and/or more precision in elasticity values.

Figure 7:
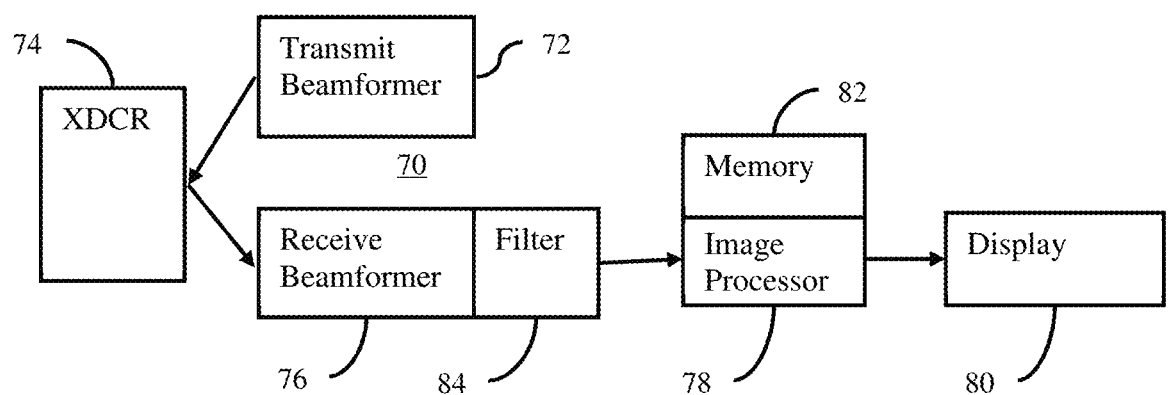
FIG. 7 is a block diagram of one embodiment of a system for clutter reduction in elasticity imaging.

The method is implemented by the system of FIG. 7 or a different system. Transmit and receive beamformers use a transducer to transmit and receive from the patient, including applying ARFI as a pushing pulse and tracking the tissue response in acts 28-38. The tissue at the ARFI focus or tissue subjected to a shear wave spaced from the focus is tracked. A filter may isolate information at different frequency bands in act 39. An image processor determines the tissue motion, combines displacements, and generates the elasticity image in acts 40-46. Different devices, such as other parts of an ultrasound scanner, may perform any of the acts.

Additional, different, or fewer acts may be provided. For example, acts 28, 30, and/or 32 are not performed. As another example, acts for configuring the ultrasound scanner, positioning the transducer, and/or recording results are provided.

The acts are performed in the order described or shown (i.e., top to bottom), but may be performed in other orders. For example, act 28 may be performed after act 38. As another example, acts 36 and 38 are performed in parallel or repeated (e.g., transmit, then receive, then transmit, then receive and so on).

In act 28, the ultrasound scanner detects reference tissue information. To determine the displacement caused by ARFI, the tissue at rest or not subjected to the ARFI is scanned. The scanning occurs prior to transmission of the ARFI in act 34 but may be performed at other times. Since the tissue response to the stress may be measured before, after, or both relative to the peak stress, the transmission for reference tissue position is performed prior to application of the stress or after the tissue returns to a relaxed state.

Acts 30 and 32 provide two examples of scanning for the reference information. In act 30, a sequence of pulses is transmitted to tissue prior to application of a stress and measurement of the tissue response to the stress. The sequence is the same as provided in act 36, such as being a sequence of pulses all having a same frequency band and center frequency. One set of N pulses is transmitted before ARFI is applied and is used to acquire reference data for displacement estimation. N may be any positive integer for each spatial location or group of spatial locations.

In act 32, reference information is received. Electrical signals generated by the transducer in response to echoes from the transmissions are received. The signals are separated by frequency band, such as by filtering, demodulation and filtering, and/or pulse phasing (inversion). In-phase and quadrature (IQ) pairs of beamformed samples for each separable signal are generated. Alternatively, the reference information is not separated by frequency component.

The beamformed data without detection is used as the reference. In other embodiments, the separated signals are used to detect reference tissue information. Any type of detection may be used, such as a B-mode detection of the intensity. The detected information is responsive to the transmitting prior to application of the stress in act 30. The tissue information is detected separately for different frequencies. Alternatively, tissue information is detected based on an average of different frequencies or based on one frequency.

In act 34, the ultrasound scanner uses the transducer to apply stress to the tissue. For example, ARFI focused at the region of interest or a point is transmitted. When ARFI is applied to a focused area, the tissue responds to the applied force by moving. Relative to an original location or relaxed state, tissue is displaced. At each given spatial location, this displacement increases and then recovers to zero, resulting in a temporal displacement profile. The tissue properties affect the displacement.

The ARFI may be generated by a cyclical pulsed waveform of any number of cycles (e.g., tens or hundreds of cycles). For example, ARFI is transmitted as a pushing pulse with 100-1000 cycles. The transmitted acoustic wave propagates to the region of interest, causing a deposition of energy and inducing tissue displacement.

Acts 36 and 38 occur after the radiation force is applied and while the tissue is responding to the stress. For example, transmission and reception occur after application or change in the stress and before the tissue reaches a relaxed state. The detection of motion in act 40 occurs in real-time with the reception of act 38. Alternatively, the detection of act 40 is performed from stored signals after the tissue reaches the relaxed state.

The response of tissue at scan lines for receive beams is detected. Ultrasound data is received in response to transmissions of ultrasound. The transmissions and receptions are performed for a single spatial location (e.g., a point adjacent to a focal point of the applied stress), along a line, over an area, or over a volume. A sequence of transmissions and receptions are provided for each spatial location to track over time. Using reception of multiple receive beams in response to each tracking transmission, data for a plurality of laterally spaced locations and/or depths may be received simultaneously.

In act 36 for tracking, the ultrasound scanner transmits a sequence of transmit beams. A plurality of ultrasound signals is transmitted to the tissue responding to the stress. The signals of the plurality are transmitted in separate transmit events. A transmit event is a contiguous interval where transmissions occur without reception of echoes responsive to the transmission. During the transmitting, there is no receiving. Where a sequence of transmit events is performed, a corresponding sequence of receive events is also performed in act 38. A receive event is performed in response to each transmit event and before the next transmit event.

For a transmit event, a transmit beam is formed. Each transmit beam has a frequency response. For example, a transmit beam is formed by a 2.0 MHz pulse of 2 cycles. The spectrum of the pulse provides an energy peak at 2.0 MHz with no other peaks within 10 or 20 dB down at another frequency. Any bandwidth may be provided. This transmit frequency band is a fundamental frequency band.

The pulses to form the transmit beams are of any number of cycles. For example, three or more cycles may be used. A greater number of cycles may reduce the bandwidth of the pulses, allowing more complete frequency separation on receive. Any envelope, type of pulse (e.g., unipolar, bipolar, or sinusoidal), or waveform may be used.

For clutter reduction, the sequence of transmit beams may all have a same center frequency and bandwidth. For example, each transmission in the sequence has a 2.0 MHz center frequency with a same pulse or bandwidth. Where pulse inversion or other phasing is used, different transmit pulses and corresponding beams may have different phases and/or maximum amplitudes. For example, the transmit pulses in the sequence are 180 degrees out-of-phase (e.g., 0 degrees, 180 degrees, 0 degrees, 180 degrees . . . ). A repeating pattern of the different pulses is used. Any pattern may be used, such as an every other or every third pattern. Any number of different transmit pulses may be used in the sequence.

Figure 2:
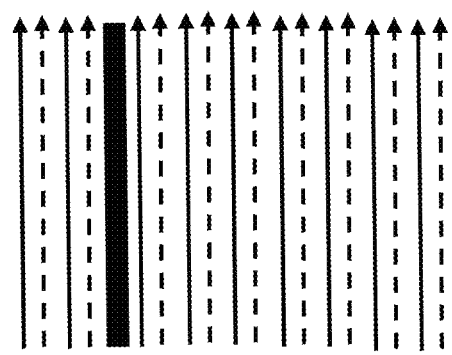
FIG. 2 illustrates an example sequence of transmit pulses with different polarities.

FIG. 2 shows an example of a sequence of ultrasound pulses having two different polarities. Each solid arrow represents a transmit beam with a pulse having one phase (e.g., pulses starting at a low voltage or 0 degree phase), and each dashed arrow represents a transmit beam with a pulse having another phase (e.g., pulses starting at a high voltage or 180 degree phase). The solid block represents the ARFI transmission of act 34, so FIG. 2 shows the sequence of transmit beams with alternating phases of pulse inversion both before and after ARFI, such as implementing both of acts 30 and 36. Any number of transmit beams may be used before and/or after the ARFI. Any harmonic imaging transmit sequence may be used.

In act 38, the transducer receives ultrasound echoes in response to each transmit event. The transducer converts the echoes to receive signals, which are receive beamformed into ultrasound data representing one or more spatial locations. The ultrasound scanner receives a sequence of receive signals where receive beams are received in response to each of the transmit beams in the transmit sequence.

The reception is interleaved with the transmission of the sequence. For each transmit event, a receive event occurs. The receive event is a continuous interval for receiving echoes from the depth or depths of interest. The receive event occurs after ceasing the transmit event. After the transducer completes generation of acoustic energy for a given transmission, the transducer is used for reception of the responsive echoes. The transducer is then used to repeat another transmit and receive event pair for the same spatial location or locations, providing the interleaving (e.g., transmit, receive, transmit, receive, . . . ) to track the tissue response over time.

FIG. 2 shows a pulse sequence for two-pulse harmonic imaging for radiation force-based elasticity imaging. The transmit and receive operations are interleaved. The transmit operations for the different polarity transmit pulses are interleaved, so the corresponding receive operations for the different polarity transmits are interleaved.

The ultrasound scanner transmits a sequence of first ultrasound pulses having a first relative phasing to other pulses. In this example, every other transmit pulse has the same phasing. In response to each of these transmit pulses, the ultrasound scanner receives first ultrasound echoes. Echoes are received in response to each transmission, so a sequence of first ultrasound echoes are received interleaved with the transmissions of the first ultrasound pulses. In the example of FIG. 2, this transmit event, then receive event for a given phase occurs nine times. A receive event occurs in between each transmit event represented by an arrow in FIG. 2, so receipt of the first ultrasound echoes for one event occurs prior to transmission of the next second ultrasound pulse.

The ultrasound scanner also transmits a sequence of second ultrasound pulses at a second phase. The second phase is different from the first phase, such as by 180 degrees (opposite polarity). The ultrasound scanner transmits a sequence of the second ultrasound pulses having a second relative phasing. In this example, every other transmit pulse has the same second phase. The second ultrasound pulses are transmitted in separate transmit events (i.e., separated by receive events) from each other and the transmit events for the first ultrasound pulses.

In response to each of these second transmit pulses, the ultrasound scanner receives second ultrasound echoes. Echoes are received in response to each second transmission, so a sequence of second ultrasound echoes are received interleaved with the transmissions of the second ultrasound pulses. A sequence of second ultrasound echoes are received for the sequence of second ultrasound pulses. In the example of FIG. 2, this transmit event, then receive event for a given phase occurs nine times. A receive event occurs in between each transmit event represented by an arrow in FIG. 2, so receipt of the second ultrasound echoes for one event occurs prior to transmission of the next first ultrasound pulse.

In alternative embodiments, the sequence of tracking pulses uses identical pulses throughout. Rather than varying phase and/or amplitude, the same phase and amplitude are used for each transmit event for tracking tissue motion from a given ARFI.

In act 39, a filter or image processor isolates different frequency components of the ultrasound echoes. The beamformed signals are filtered to determine components at different frequency bands. Any bandwidth and/or center frequencies may be used. The frequency bands may or may not overlap.

In one embodiment, the harmonic and fundamental bands are used. The fundamental (i.e., first harmonic) is the frequency band and center frequency of the transmit pulse. The harmonic is any fractional (e.g., ½) or integer harmonic other than the first harmonic (i.e., fundamental). The harmonic is a frequency band where a majority of the signal content is from signal generated by propagation and/or echo rather than being transmitted. Some fundamental may be in the harmonic, but a majority of the signal (e.g., area under the spectrum) is harmonic. Similarly, some harmonic may be in the fundamental, but a majority of the signal is fundamental.

The isolation may not be absolute. A 10 dB or greater reduction of frequencies outside the frequency band is provided for isolation. In alternative embodiments, the isolation is sufficient that component signals are responsive to different levels of clutter.

In one embodiment, the isolation is by pulse inversion. By summing signals responsive to transmit pulses with opposite phase, the odd harmonics and/or fundamental frequency components are reduced or cancel out. The resulting second harmonic and/or even harmonic information provides information as one frequency component. By subtracting the signals responsive to the transmit pulses with opposite phase, the even harmonics and/or second harmonic are reduced or cancel out. The resulting fundamental (i.e., transmit pulse frequency band and/or center frequency) and/or odd harmonic information provides information as another frequency component. This addition and subtraction is repeated through the sequence (e.g., moving time window of two transmit-receive events), providing a sequence of signals at the different frequency components.

Other pulse inversion, such as using three or more transmit pulses and a corresponding three or more receive signals, to isolate information at desired frequencies may be used. For example, a cubic fundamental is isolated using three different relative phases and amplitudes for transmit and combining the corresponding receive signals. As another example, the receive signals at the fundamental frequency band use receive signals from a given transmit pulse without subtraction or addition.

In another embodiment, the receive signals are filtered into bands for different frequencies. To provide information at more than one frequency band, the receive band is separated into two or more sub-bands. The receive signals and/or beamformed samples are filtered to isolate information at different center frequencies and/or frequency bands. For example, the receive signals responsive to a 1-2 MHz transmit pulse are at 1-3 MHz (center frequency of 2 MHz), so are filtered into two bands of 1-2 MHz (center frequency of 1.5 MHz) and 2-3 MHz (center frequency of 2.5 MHz). One of the frequency components includes at least part of the band outside of the fundamental or transmit band.

In the case of radio-frequency (RF) data, multiple band-pass filters are applied to the raw receive signals. For in-phase and quadrature (IQ) data, complex low pass filters are applied to the demodulated or downshifted signals. Other filtering may be used.

In act 40, the image processor determines displacements from the different frequency components. For example, displacements are separately determined for harmonic components of the ultrasound echoes and fundamental components of the ultrasound echoes.

The ultrasound scanner determines tissue motions in act 40. Tissue motion is detected as a displacement in one, two, or three dimensions. For example, the displacement of tissue along scan lines is determined. Motion responsive to the applied force, generated shear wave or other wave may be detected. The tissue motion is detected at different times. The different times correspond to the different tracking scans (i.e., transmit and receive event pairs).

The displacement is measured with beamformed samples (e.g., I/Q or RF data for scan lines), but tissue data (e.g., B-mode data detected from beamformed samples) or flow data (e.g., velocity estimated from beamformed samples) may be used.

Tissue motion is detected by estimating displacement relative to the reference tissue information. Correlation, cross-correlation, phase shift estimation, minimum sum of absolute differences or other similarity measure is used to determine the displacement between scans (e.g., between the reference and the current). For example, each IQ data pair is correlated to its corresponding reference to obtain the displacement along one dimension (e.g., along the scan line). Data representing a plurality of spatial locations is correlated with the reference data. As another example, data from a plurality of spatial locations (e.g., along the scan lines) is correlated as a function of time. For each depth or spatial location, a correlation over a plurality of depths or spatial locations (e.g., kernel of 64 depths with the center depth being the point for which the profile is calculated) is performed. The spatial offset with the highest or sufficient correlation at a given time indicates the amount of displacement.

The monitoring is performed for any number of scan lines. For example, four, eight, sixteen, thirty-two, sixty-four, or other number of receive beams are formed in response to each transmission. In other embodiments, only a single receive beam or other numbers of receive beams are formed in response to each transmission.

For each location, the displacement as a function of time is determined. After transmitting the acoustic radiation force to induce displacement, transmissions configured for B-mode imaging are performed repetitively along a single scan line, and receptions along any number of adjacent scan lines are performed. Each repetition monitors the same region or locations for determining tissue response for those locations. By repeating the transmitting of the ultrasound pulses and the receiving of the ultrasound echoes over the time, the displacements over the time are determined. The tracking is repeated. The repetition is for different transmit and receive events. Any number of M repetitions may be used, such as repeating about 50-100 times. The repetitions occur as frequently as possible while the tissue recovers from the stress, but without interfering with reception. The tissue temporal displacement profile is obtained by repeatedly transmitting to and receiving signals from the same target area in a similar way as the Doppler method does.

The displacements are determined separately for the receive signals at different frequencies. Two or more time sequences of displacements are determined for a given location from the two or more time sequence of received signals at a respective two or more center frequencies or frequency bands. Tissue motion is detected from the signals at the different frequencies. Displacements are estimated for each frequency band, such as displacements over time for a fundamental component and for a second harmonic component. Displacements are independently determined from the different frequency components by using the isolated signals for the different frequency components. For example, correlation of beamformed samples (e.g., I/Q data) isolated for the second harmonic with reduced information from a fundamental component of the received signals is used to determine displacements from the reference information at the second harmonic, and correlation of beamformed samples isolated for another frequency component (e.g., fundamental or transmit frequency) with reduced information from the second harmonic of the received signals is used to determine displacements from the reference information at the other frequency.

Displacement profiles as a function of time for different locations and/or as a function of location for different times are determined. Any number of locations and/or times may be used. For each location and time, multiple displacements corresponding to the different frequency bands are provided.

In act 41, the image processor forms combined displacements. For each location and/or time, the displacements from the different frequency bands are combined. In one embodiment, the displacements from the harmonic frequency component are combined with the displacements from the other frequency (e.g., fundamental) component.

The combination acts to reduce clutter. The combination weights based on spatial region from which the received signals originated where the harmonic or other frequency components are stronger. Rather than averaging, such as for frequency compounding to reduce speckle, the combination uses the different strengths of clutter response to reduce clutter. The weighting in the combination to reduce clutter uses a difference in proportion of the signal from a body wall or other structure to signal from the tissue of interest (e.g., liver).

Any combination function to cancel out clutter may be used. A difference represented by subtraction and/or a ratio is used to reduce the clutter. For example, the difference in displacements tracked with the harmonic signal and displacements tracked with the fundamental signal is found, and then that difference is subtracted from the displacements tracked with the harmonic signal. This combination is represented by:

$$u_c = u_h - (u_f - u_h), \quad (1)$$

where $u_c$ is the combined displacement, $u_f$ is the displacement tracked with the fundamental signal, and $u_h$ is the displacement tracked with the harmonic signal. Weights may be added to any of the terms, such as weighting the difference, the harmonic displacement, and/or the fundamental displacement. Tracking the fundamental may be used, where the difference is subtracted or added to the fundamental displacement. The difference may be of the fundamental displacement from the harmonic. A ratio may be used. Constants or other variables may be added.

In the combined displacement estimate of equation 1 when applied to shear wave imaging of the liver, the signal from the body wall is reduced compared to the signal from within the liver. Additionally, in media with low noise, the displacement signals are preserved since the displacements tracked with fundamental signals and the displacements tracked with harmonic signals are the same or similar. The clutter filtering adapts so that patients with higher noise (e.g., higher BMI) have more clutter removed.

The combination provides a combined displacement for each location and time. Temporal and/or spatial displacement profiles are provided for generating an elasticity image using any elasticity estimation.

In act 42, the ultrasound scanner generates an image of elasticity. The elasticity and resulting image are based on the tissue motions determined from the displacements after clutter filtering (e.g., after combination of displacements from harmonic and fundamental frequency bands). Where the displacements calculated using information from the different frequencies are compounded, the elasticity estimated from the displacements includes the clutter reduction. Elasticities are output for one or more locations and are based on some combination of displacements from information having different relative clutter contribution.

The generation of the image of act 42 is represented as estimating the elasticity in act 44 and creating the image in act 46. Other representations may be used to derive output values used for imaging from the combined displacements.

In one embodiment of act 44, the time of the occurrence of the peak combined displacement is used to represent the elasticity of the tissue for that location. The time of the peak combined displacement in the displacement profile is determined at a plurality of locations and used to estimate a wave velocity, such as in shear wave velocity imaging. A plurality of repetitions of the transmit and receive events in acts 36, 38 provide samples over a period.

The peak displacement may be identified by finding a maximum combined displacement. For shear wave imaging, the temporal profile for a given location indicates detection of the shear wave. A peak in the profile, with or without temporal low pass filtering, indicates the passing of the shear wave front. In an alternative embodiment, a phase relationship between displacement profiles at different locations is used to estimate the velocity without identifying the peak displacement.

In an alternative embodiment, a curve is fit to the tissue motion samples. Any curve fitting may be used. For example, a regression is applied. Since the shear wave velocity is linear, a robust linear regression with automated outlier detection may indicate the shear wave velocity. The ultrasound data for all the sample points in the region of interest is plotted for distance as a function of time or by time and distance. The linear regression is applied to the plot or data, providing a line fit to the data. In another example, a spline interpolation is used. After sorting the data of the profiles, cubic spline interpolation is used to reconstruct the final temporal displacement profile. In other embodiments, a Fourier transform is used. The curve is identified in the frequency domain after removing components at undesired frequencies. The inverse transform provides the time curve.

The tissue response, such as the peak, may be used as a result. Shear velocity is obtained by determining a time from generation of the shear wave until detection of the shear wave at a different location. The distance is known from the scan line spacing (i.e., the transmit beam position for generating the shear wave and the receive beam position for detecting the shear wave). The time is known from the relative time between generation and detection of the shear wave.

As another example, a feature is extracted from the temporal profiles. Principal component decomposition may be used. A correlation between the different temporal profiles is performed. The lag associated with the different distances for the different temporal profiles provides the shear velocity. Alternatively, a wavelet analysis may be performed. A wavelet transform is applied to the temporal profiles to identify a peak or other characteristic corresponding to the shear wave. A velocity value is identified from the travel time of the peak to each spatial location.

Alternatively, further calculations are performed for the estimation of elasticity. A tissue mechanical property may be characterized as a function of the tissue response. The peak and its temporal location in the temporal displacement profile may be used to characterize tissue's mechanical property, such as strain, strain rate, elasticity, viscosity, impedance, or others. Any elasticity information may be estimated.

The elasticity at one location is estimated. The single elasticity value may be an average of values from surrounding locations. To create a spatial image in act 46, the elasticities at different locations are estimated in act 44. The transmitting of the ultrasound pulses, the receiving of the ultrasound echoes over the time, the determining of displacements, and the estimating for different spatial locations is repeated. The resulting estimates of elasticity for different locations are used to generate an elasticity image representing elasticity along one, two, or three dimensions. The output elasticity for the different spatial locations is used in elasticity imaging.

The transmission of the ARFI pulse may or may not be repeated. To monitor a larger region, additional receive beams may be formed in response to the monitoring transmit beam. Alternatively, another ARFI pulse is transmitted and the transmit beams and receive beams are provided at different spatial locations. In a 6 mm×10 mm monitoring region example, 36 receive scan lines may be provided. At four receive beams per transmit beam, the process is repeated for different lateral spacing nine times. For each receive beam location, a time profile of motion information is provided, represented by the ultrasound data.

The samples may be acquired for one depth. Alternatively, the sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 samples for 5 mm or 400 samples for 10 mm.

Ultrasound data representing different locations in the region of interest is obtained. Tissue motion for each location is determined as a function of time. For each location, the motion information represents the response at different times, providing a temporal profile. Other scanning, monitoring, or techniques may be used to obtain ultrasound data to estimate an elasticity image.

In act 46, the ultrasound scanner generates an image of an output elasticity. In one embodiment, the image is a shear wave velocity image. The shear wave velocity as a function of location is output. Other elasticity information may be used. In alternative or additional embodiments, the elasticity is output as a value (e.g., shear wave velocity for a selected point). A graph, table, or chart of elasticities may be output as the image. Due to the adaptive clutter filtering, any output elasticity may be more accurate, representing elasticity with less contribution from clutter.

Figure 3:
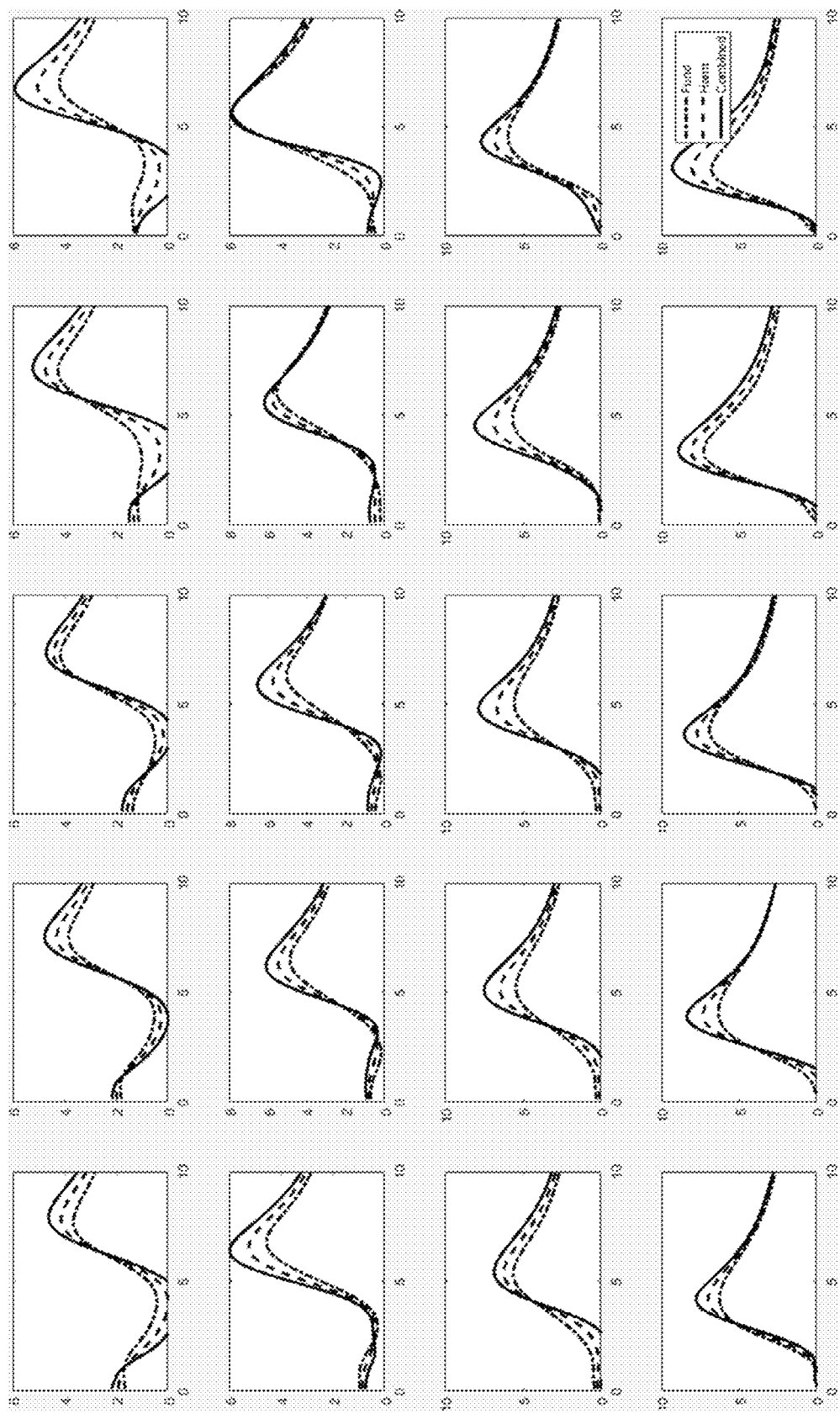
FIG. 3 shows example displacements over time of the fundamental, harmonic, and combined fundamental and harmonic at different azimuth locations in a phantom.

FIG. 3 shows displacement profiles over time for twenty different parallel receive beams in a phantom. The displacement profiles are determined from transmitting an ARFI, and then tracking over time using simultaneously formed receive beams for twenty receive scan lines at each time. The displacement profiles for the fundamental band contain primarily odd harmonics and primarily the fundamental component relative to other odd harmonics. Inverse polarity tracking pulses with subtraction of received signals is used to isolate at the fundamental (i.e., transmit) frequency band. The displacement profiles for the harmonic contain primarily even harmonics and primarily the second harmonic relative to other even harmonics. Inverse polarity tracking pulses with addition of received signals is used to isolate at the second harmonic (i.e., non-transmitted) frequency band. The displacement profile for the combined displacements is formed using the harmonic and fundamental displacements and equation 1. The phantom is similar to low BMI, so the fundamental and harmonically tracked displacements are nearly identical. Thus, the combined displacement signal is very similar as well.

Figure 4:
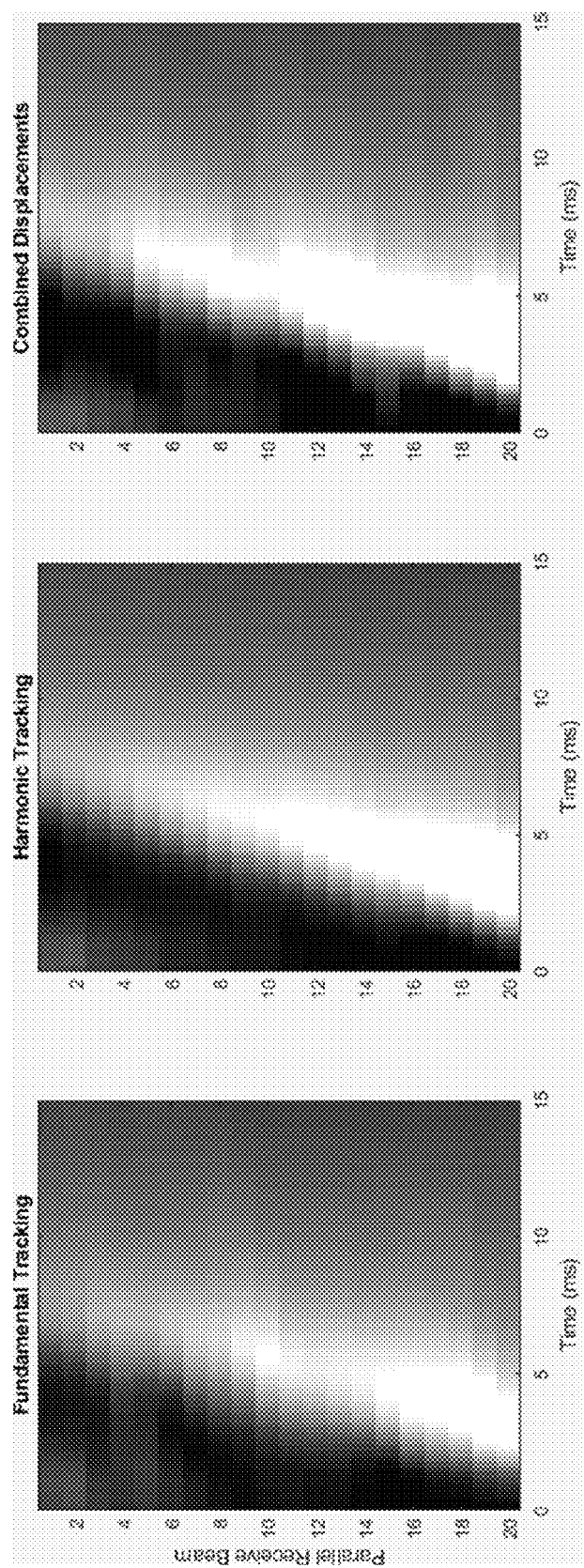
FIG. 4 shows example images of azimuth location as a function of time for displacements at the fundamental, harmonic, and combined fundamental and harmonic of FIG. 3.

FIG. 4 shows the displacement profiles of FIG. 3 with displacement mapped to greyscale, providing displacement as a function of scan line and time. Since there is little clutter, the displacement profiles and timing of maximum displacement are similar.

Figure 5:
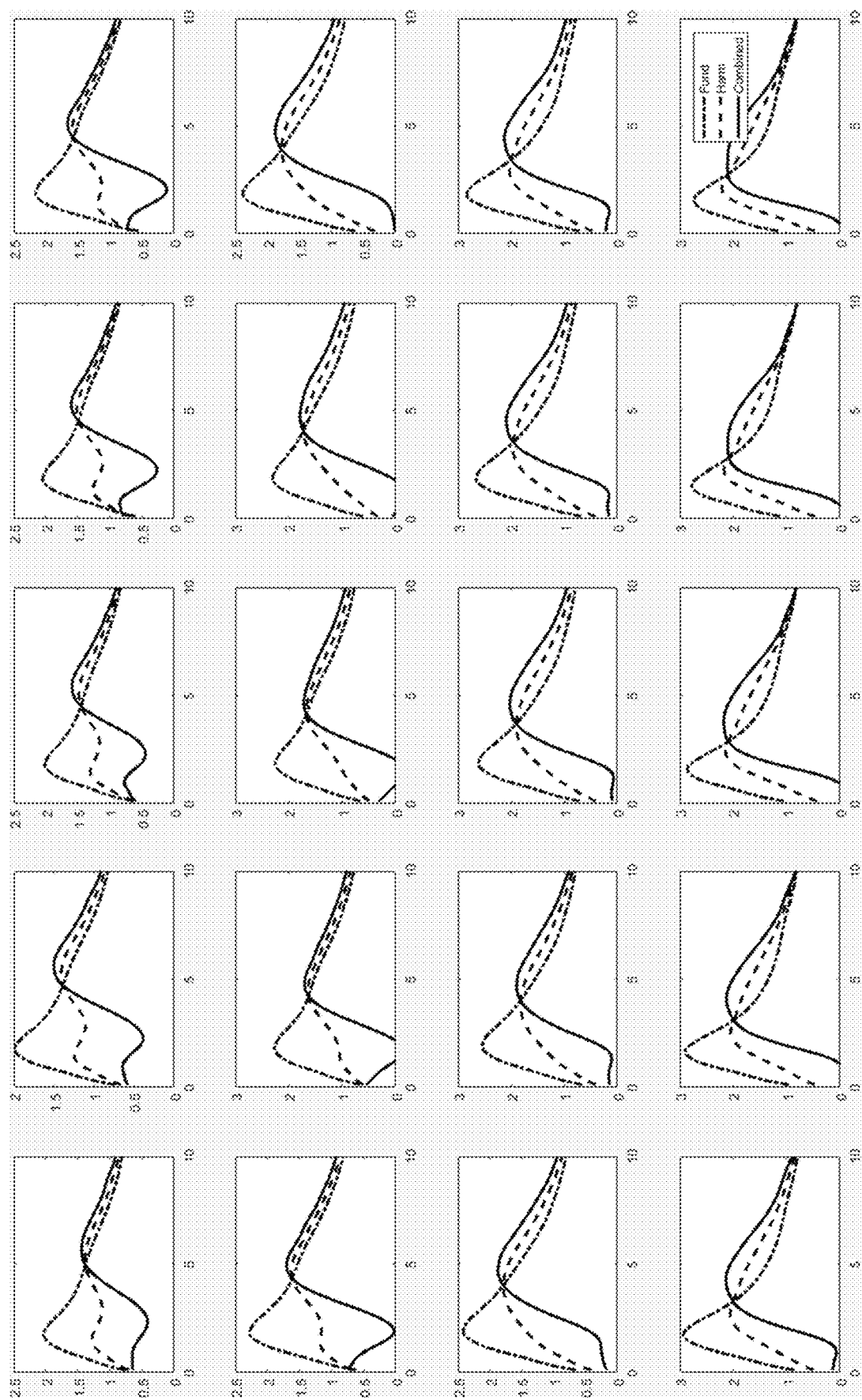
FIG. 5 shows example displacements over time of the fundamental, harmonic, and combined fundamental and harmonic at different azimuth locations in a high body-mass index patient.
Figure 6:
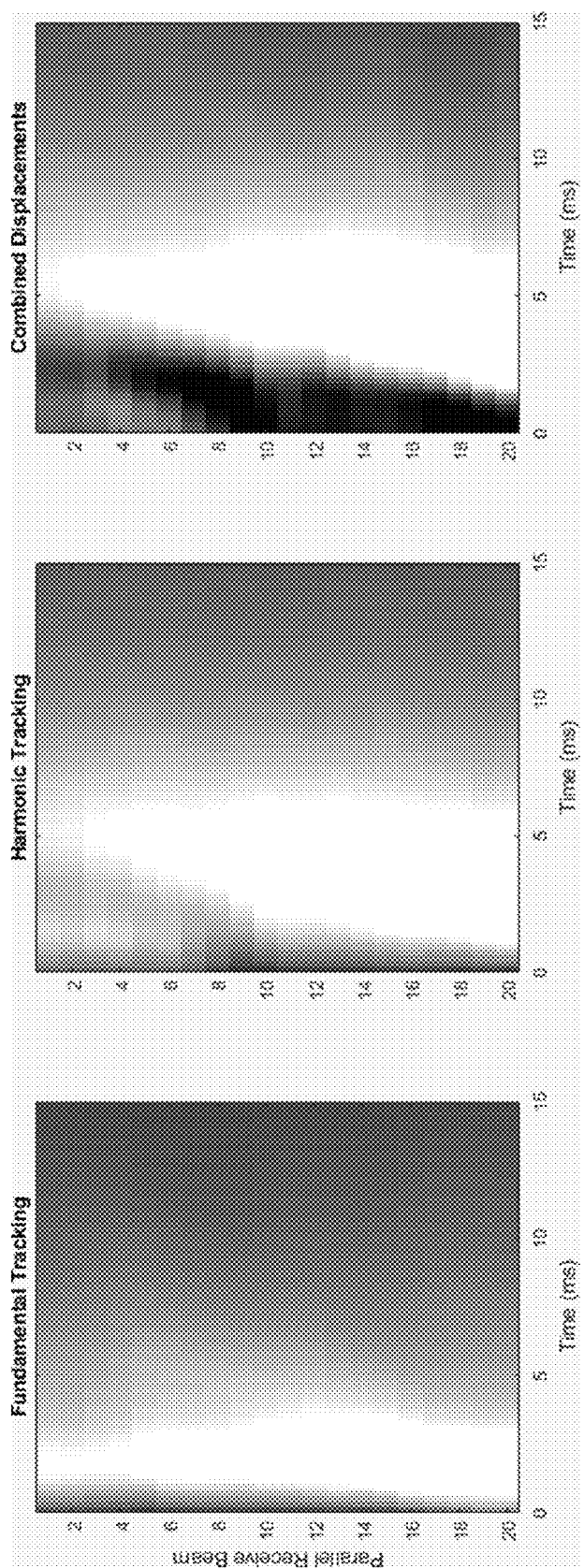
FIG. 6 shows example images of azimuth location as a function of time for displacements at the fundamental, harmonic, and combined fundamental and harmonic of FIG. 5.

FIGS. 5 and 6 shows the same approach for FIGS. 3 and 4, but with a high BMI patient instead of the phantom. In this patient, the peak in the displacement profile of the fundamental occurs earlier than for the harmonic, especially for lateral or azimuth receive scan line locations spaced from the shear wave origin (origin at scan line 0, furthest scan line being scan line 20). The signal from the body wall (i.e., clutter) causes the peak in the displacement earlier in time at the further azimuthal locations. The clutter, even in the harmonic, may make the time of peak displacement less precise. The shear wave signal within the liver is emphasized over the body wall signal in the combined displacements, at least partially correcting the timing of the peak.

FIG. 7 shows one embodiment of a system 70 for clutter reduction in acoustic radiation force impulse or elasticity imaging. Information from different frequencies (e.g., fundamental and second harmonic) are used to adaptively clutter filter by removing a difference due to clutter content. The system 70 implements the method of FIG. 1 or other methods.

The system 70 is a medical diagnostic ultrasound imaging system or ultrasound scanner. In alternative embodiments, the system 70 is a personal computer, workstation, PACS station, or other arrangement at a same location or distributed over a network for real-time or post acquisition imaging, so may not include the beamformers 12, 16 and transducer 74.

The system 70 includes a transmit beamformer 72, a transducer 74, a receive beamformer 76, an image processor 78, a display 80, a memory 82, and a filter 84. Additional, different or fewer components may be provided. For example, a user input is provided for manual or assisted selection of display maps, selection of tissue properties to be determined, region of interest selection, selection of transmit sequences, or another control.

The transmit beamformer 72 is an ultrasound transmitter, memory, pulser, waveform generator, analog circuit, digital circuit, or combinations thereof. The transmit beamformer 72 is configurable to generate waveforms for a plurality of channels with different or relative amplitudes, delays, and/or phasing.

The transmit beamformer 72 generates and causes transmission of pulses having a center frequency and bandwidth, the fundamental frequency band. The transmit beamformer 72 is configured to transmit a sequence of pulses. For a given pulse or transmit beam, the transmit beamformer 72 generates the pulse as having a phase. The pulse forms the transmit event for a responsive receive operation. In the sequence, different transmit pulses have different phase, such as a sequence of inverted polarity pulses (e.g., every other pulse with opposite or 180 degree different phase). The pulses are generated repetitively with gaps in time for receive operation after each pulse. For example, the sequence of FIG. 2 is used. In alternative embodiments, the same phase is used for each pulse. The same or different center frequencies and/or bands may be used for different pulses.

Upon transmission of acoustic waves from the transducer 74 in response to the generated waves, one or more beams are formed. For elasticity imaging, the same region is scanned multiple times. In Doppler imaging and elasticity estimation, the sequence may include multiple beams along a same scan line before scanning an adjacent scan line. An ARFI transmission may be generated by the transmit beamformer 72 as part of the sequence. By repeating the elasticity estimation process for different locations, sequences of transmit beams are generated to scan a two or three-dimensional region. Sector, vector, linear, or other scan formats may be used. The transmit beamformer 72 may generate a plane wave or diverging wave for more rapid scanning.

The transmit beams are formed at the same or different amplitude levels. Amplifiers for each channel and/or aperture size control the amplitude of the transmitted beam. The ARFI transmit beams may have greater amplitudes than for imaging or detecting tissue motion. Alternatively or additionally, the number of cycles in the ARFI pulse or waveform used is typically greater than the pulse used for tracking (e.g., 100 or more cycles for ARFI and 1-6 cycles for tracking).

The transducer 74 is a 1-, 1.25-, 1.5-, 1.75-, or 2-dimensional array of piezoelectric or capacitive membrane elements. The transducer 74 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The transmit beamformer 72 and receive beamformer 76 connect with the same elements of the transducer 74 through a transmit/receive switch or multiplexer. The elements are shared for both transmit and receive events. One or more elements may not be shared, such as where the transmit and receive apertures are different (only overlap or use entirely different elements).

The receive beamformer 76 includes a plurality of channels with amplifiers, delays, and/or phase rotators, and one or more summers. Each channel connects with one or more transducer elements. The receive beamformer 76 applies relative delays, phases, and/or apodization to form one or more receive beams in response to a transmission. Dynamic focusing may be provided. The receive beamformer 76 may include channels for parallel receive beamforming, such as forming two or more receive beams in response to each transmit event. The receive beamformer 76 outputs beam summed data, such as IQ values, for each beam.

The receive beamformer 76 operates during gaps in the sequence of transmit events. By interleaving receipt of signals with the transmit tracking pulses, a sequence of receive beams are formed in response to the sequence of transmit tracking beams. After each transmit tracking pulse and before the next transmit pulse, the receive beamformer 76 receives signals from acoustic echoes. Dead time during which receive and transmit operations do not occur may be interleaved to allow for reverberation reduction.

The receive beamformer 76 outputs beam summed data representing spatial locations at a given time. Data for a single location, locations along a line, locations for an area, or locations for a volume are output. The data may be for different purposes. For example, different scans are performed for B-mode or tissue data than for shear wave velocity estimation. Data received for B-mode or other imaging may be used for estimation of the elasticity image. The shear wave at locations spaced from a focus of the pushing pulse or the tissue response at the focus are monitored to determine elasticity.

The receive beamformer 76 may include the filter 84. Discrete hardware (e.g., resistors, capacitors, inductors, buffers, multipliers, and/or summers) may be used. Alternatively, the filter 84 is a separate component or is implemented by the image processor 78. The filter 84 may be positioned to filter beamformed data output by the receive beamformer 76, to filter radio frequency data input to the receive beamformer 76, or to filter other data at other points along the ultrasound processing. The filter 84 may include parallel paths for filtering the same receive signals or beamformed data into different frequency bands or sub-bands. The filter 84 is programmable.

The filter 84 isolates information at desired frequency bands and/or reduces the contribution of information at frequencies outside the desired frequency band. In one embodiment, the filter is a buffer, summer, subtractor, and/or combinations thereof. For pulse inversion or other multi-phase transmit, receive signals from different receive events are combined to isolate particular frequency components. Summing receive signals from opposite phase transmissions may reduce odd harmonics including the fundamental, leaving information at the second or other even harmonics. Subtracting receive signals from opposite phase transmissions may reduce even harmonics including the second harmonic, leaving information at the fundamental. Alternatively and/or additionally, the filter 84 is a band pass filter or demodulator and band or low pass filter. For example, the receive signals at the fundamental are formed by band or low pass filtering receive signals without subtracting.

The filter 84 outputs information in different frequency bands for the received signals. In one embodiment, the same receive signals are used to isolate information at the fundamental frequency and at a frequency not part of the transmitted pulse (e.g., at the second harmonic). For each receive event or combination of receive events, the same filtering is applied. In an alternative or additional embodiment, the receive signals responsive to different transmit events are filtered differently.

The image processor 78 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, network, server, group of processors, data path, combinations thereof or other now known or later developed device for processing information for display from beamformed ultrasound samples. In one embodiment, the image processor 78 includes one or more detectors and a separate processor for elasticity imaging. The image processor 78 performs any combination of one or more of the acts 40-46 shown in FIG. 1.

The beamformed data is provided in two or more different frequency bands and/or having two or more center frequencies. The clutter content for each band is different. Prior to or after detection, the image processor 78 is configured to detect displacements of tissue responding to acoustic radiation force from the information in the different frequency bands and/or center frequencies (e.g., from the even harmonic and the fundamental). The displacements are detected using correlation or other measure of similarity performed separately and/or independently for the different frequency bands or center frequencies. By spatially offsetting a tracking set of data relative to a reference set of data in one, two, or three-dimensional space, the offset with the greatest similarity indicates the displacement of the tissue. Other displacement detection may be used. A displacement profile or displacement over time may be created.

The image processor 78 is configured to estimate elasticity. For each spatial location sampled in tracking, the image processor 78 determines a mechanical property of tissue or characteristic of the wave propagation at that location. For example, the shear wave velocity is calculated. The relative phase in the displacement profiles from an adjacent location and/or timing of peak in the displacement profile at the location of interest is identified and used with the geometry of the location relative to the shear wave origin and timing of the shear wave generation to calculate the velocity.

The elasticity is estimated from a compound of the displacements from the different frequencies (e.g., from even harmonic and fundamental frequencies). A difference of the displacements from the different frequencies indicates relative amount of clutter, which is removed from one of the other displacements. For example, equation 1 is used. By estimating elasticity from the compounded displacements of harmonic and fundamental receive signals, clutter may be adaptively reduced.

The image processor 78 outputs an elasticity for each of one or more locations. The elasticity is more precise or accurate due to clutter removal.

The image processor 78 generates display data, such as graphic overlays and images. The display data is in any format, such as values before mapping, gray scale or color-mapped values, red-green-blue (RGB) values, scan format data, display or Cartesian coordinate format data, or other data. The image processor 78 outputs elasticity appropriate for the display device 20.

The display device 20 is a CRT, LCD, projector, plasma, printer, or other display for displaying elasticity (e.g., shear velocity), graphics, user interface, two-dimensional images, or three-dimensional representations. The display device 20 displays ultrasound images, the elasticity, and/or other information. For example, the display 80 outputs tissue response information, such as a one, two, or three-dimensional representation of the elasticity. Elasticities for different spatial locations form an image. Other images may be output as well, such as overlaying the elasticity as a color-coded modulation on a gray scale B-mode image.

In one embodiment, the display device 20 outputs an image of a region of the patient, such as a two-dimensional elasticity, Doppler tissue, or B-mode image. The image includes a location indicator for the elasticity. The location relative to the imaged tissue for which an elasticity value is calculated is shown. The elasticity is provided as an alphanumeric value on or adjacent the image of the region. The image may be of the alphanumeric value with or without spatial representation of the patient. Alternatively or additionally, elasticity is determined for a plurality of locations and the image pixels are modulated as a function of the elasticity for spatially representing shear velocity.

The image processor 78 operates pursuant to instructions stored in the memory 82 or another memory. The memory 82 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for clutter reduction in elasticity imaging with an ultrasound scanner, the method comprising:
   transmitting acoustic radiation force from a transducer of the ultrasound scanner to tissue of a patient, the tissue responding to stress caused by the acoustic radiation force;
   transmitting by the ultrasound scanner a sequence of ultrasound pulses;
   receiving by the ultrasound scanner ultrasound echoes responsive to the ultrasound pulses of the sequence;
   isolating harmonic and fundamental components of the ultrasound echoes;
   determining first displacements of the harmonic components of the ultrasound echoes and second displacements of the fundamental components of the ultrasound echoes;
   forming combined displacements from a subtraction of a difference from the first displacements, the difference being of the first displacements from the second displacements;
   estimating an elasticity from the combined displacements; and
   generating an image of the elasticity.

2. The method of claim 1 further comprising:
   detecting reference tissue information prior to transmitting the acoustic radiation force; and
   determining the first and second displacements as a function of the reference tissue information.

3. The method of claim 1 wherein isolating comprises isolating the harmonic component from summing the ultrasound echoes from inverted ones of the ultrasound pulses and isolating the fundamental component from subtracting the ultrasound echoes from the inverted ones of the ultrasound pulses.

4. The method of claim 1 wherein determining the first and second displacements comprises detecting motion responsive to a shear wave.

5. The method of claim 1 wherein determining the first and second displacements comprises determining first and second displacement profiles of displacement as a function of time and location.

6. The method of claim 1 wherein forming comprises weighting the difference, the first displacements, the second displacements, and/or a combination thereof.

7. The method of claim 1 wherein estimating comprises determining a peak displacement.

8. The method of claim 1 wherein generating the image comprises generating a shear wave velocity image, the elasticity comprising a shear wave velocity.

9. The method of claim 1 further comprising repeating the transmitting of the ultrasound pulses, the receiving of the ultrasound echoes over the time, the determining, the forming, and the estimating for different spatial locations, and wherein generating the image comprises generating the image representing the elasticity as a function of the different spatial locations.

\* \* \* \* \*